United States Patent
Chung et al.

(10) Patent No.: US 6,906,524 B2
(45) Date of Patent: Jun. 14, 2005

(54) ELECTRONIC CIRCUIT FOR ION SENSOR

(75) Inventors: Wen-Yaw Chung, Taoyuan Hsien (TW); Alfred Krzyskow, Pruszk (PL); Yeong-Tsair Lin, Yun Lin Hsien (TW); Dorota Genowefa Pijanowska, Nieporet (PL); Chung-Huang Yang, Ching Men Hsien (TW); Wladyslaw Torbicz, Warsaw (PL)

(73) Assignee: Chung-Yuan Christian University, Chung Li (TW)

( * ) Notice: Subject to any disclaimer, the term of this patent is extended or adjusted under 35 U.S.C. 154(b) by 0 days.

(21) Appl. No.: 10/647,227

(22) Filed: Aug. 26, 2003

(65) Prior Publication Data

US 2004/0223287 A1 Nov. 11, 2004

(30) Foreign Application Priority Data

May 9, 2003 (TW) ........................................ 92112663 A

(51) Int. Cl.[7] .............................................. G01N 27/62
(52) U.S. Cl. ......................................... 324/464; 205/789
(58) Field of Search ......................... 324/464; 361/235; 204/416; 205/789

(56) References Cited

U.S. PATENT DOCUMENTS

| | | | | |
|---|---|---|---|---|
| 4,645,583 A | * | 2/1987 | Shirai et al. | 204/435 |
| 5,296,122 A | * | 3/1994 | Katsube et al. | 204/298.04 |
| 5,309,085 A | * | 5/1994 | Sohn | 324/71.5 |
| 6,624,637 B1 | * | 9/2003 | Pechstein | 324/438 |

* cited by examiner

*Primary Examiner*—Anjan Deb
*Assistant Examiner*—Timothy J. Dole
(74) *Attorney, Agent, or Firm*—Rabin & Berdo, P.C.

(57) ABSTRACT

An ion sening circuit comprises a bridge sensing circuit and a differential amplifying circuit. The bridge sensing circuit detects the ion concentration of the solution in the operation mode of constant voltage and constant current. The differential amplifying circuit compares the output of the bridge sensing circuit and a floating reference voltage, thereby the delivered voltage to the bridge sensing circuit, such that the opeation mode of constant voltage and constant current is formed accordingly. The main features of the disclosed circuit are that it grounds the reference electrode and floats the source terminal. The drawbacks of not being manufactured with intergrated circuits by CMOS technology and low benefits when applied to sensor arrays are avoided by the disclosed circuit.

19 Claims, 6 Drawing Sheets

ELECTRONIC CIRCUIT FOR ION SENSOR

BACKGROUND OF THE INVENTION

1. Field of Invention

The invention relates to an ion sensing circuit, and more particular to a circuit adopting Ion-Sensitive Field Effect Transistors that is compatible with CMOS technology and implemented by integrated circuits.

2. Related Art

Silicon-based semiconductor micro sensors are now able to react to the ion concentration (activity). The Ion-Sensitive Field Effect Transistor (ISFET), which is a micro sensing element combining electrochemistry with microelectronics technology, was introduced in the 1970s. The ISFET selectively senses the ion concentration in an electrolyte. The ISFET is a trans-resistance element, which has the features of low output impedance of MOSFET and operation of Ion Selective Electrode (ISE). The ISFET has features of rapid reaction time, high sensitivity, batch processing, small size and single chip integration. Furthermore, it can be implemented by CMOS technology. These advantages make it the first choice for VLSI electrochemistry sensing array.

Compared with MOSFET, ISFET replaces the metal or polysilicon gate with electrolytes and reference electrode. Different concentration of electrolyte components causes corresponding variations of the threshold voltage of the ISFET. Through the reaction of the sensing membrane and the electrolyte, the concentration of H+ or other ions can be acquired by sensing circuits.

Many sensing circuits based on the above concept have been proposed in the prior art. One of which is shown in FIG. 1. The sensing circuit of FIG. 1 detects the ion concentration of the solution with features of constant voltage/constant current operation mode, and floating reference electrode. The drain terminal of the transistor ISFET is connected to the output terminal of the first amplifier OP1, where a constant voltage, e.g., 0.7 volts in the figure, is fed to its positive terminal. The negative terminal is connected to the output terminal. The source terminal of the transistor ISFET is coupled with the negative terminal of the second amplifier OP2, and coupled with the ground via a resistor R. A constant voltage, e.g., 0.5 volts in the figure, is fed to the positive terminal of the second amplifier OP2. The output terminal of the second amplifier OP2 is coupled with the reference electrode Ref of the transistor ISFET. With this configuration, two constant voltages input to the two positive terminals of the amplifiers cause the source terminal S and the drain terminal D of the transistor ISFET to keep a constant drain-source voltage difference. The solution of the ion concentration creates the connection between the reference electrode Ref and gate sensing membrane (terminal G). The potential difference between the gate sensing membrane and the reference electrode Ref is determined by the ion concentration of the solution.

The sensing circuit in FIG. 1 is easy to be implemented by integrated circuits. The measured signal is the output from the amplifier OP2 connected with the reference electrode Ref.

However, once the sensing circuit in FIG. 1 is applied to multiple sensors or sensor arrays, since one reference electrode is necessary for each transistor ISFET, the increasing number of sensors leads to increasing number of reference electrodes. This is not economically viable, and is not suitable for mass production or commercial development.

The circuit in FIG. 2 adopts one sensing circuit for all the sensors, i.e., only one reference electrode is used to detect the ion concentration. The circuit in FIG. 2 is composed of a first transistor ISFET1 and a second transistor ISFET2. The drain terminals of the two transistors are connected together. The drain terminal of the transistor ISFET1 is coupled with the output terminal of the first amplifier OP1, where a constant voltage, e.g., 0.7 volts in the figure, is fed to its positive terminal. The negative terminal of the first amplifier OP1 is connected to the output terminal. The source terminals of the two transistors coupled with analog switches CH1 and CH2 respectively, which are switched by a multiplexer. The switches CH1 and CH2 are also coupled with the negative terminal of the second terminal OP2. The negative terminal is also coupled with the ground via a resistor R. A constant voltage, e.g., 0.5 volts in the figure, is fed to the positive terminal of the second amplifier OP2, whose output terminal is coupled to the reference terminal. The two constant voltages input to the two positive terminals of the amplifiers cause the source terminal and the drain terminal of the transistor ISFET to keep a constant voltage difference.

The main advantages of the circuit in FIG. 2 are reduced chip size and power consumption. However, the problems of the conductivity of the switches, the rising temperature upon switching and noise interference need to be solved. Furthermore, only one ISFET operates at one time. Sufficient stable time is needed before switching to the next ISFET so all the sensors cannot operate at the same time. The situation is more serious when the number of ISFETs in the sensor array increases. The detected signal implies the drift error of the ISFET owing to the switching time for completing the detection by ISFETs.

The multiple sensing circuit presented in FIG. 2 has essential drawbacks. The supplying voltage is multiplexed by CH1 and CH2 from ISFET1 to ISFET2 and both ISFETs cannot be supplied simultaneously. This may cause instability of the output signal Vout due to transient processes resulting from the switching. Another drawback is increasing of measuring time resulting from the serial mode of operation and the above-mentioned transient processes.

Therefore, for overcoming of the above-mentioned drawbacks, another circuit is proposed in FIG. 3. The configuration of this circuit involves grounding the reference electrode and a bridge-type circuit with a floating voltage source.

The bridge-type configuration includes a current source Iref, a constant voltage source that is generated together with a variable resistor Rv, and an operational amplifier OP. The Zener diode ZN1 provides a specific reference voltage. The operational amplifier OP, the resistor Ra, Rb, and Rc, and the ISFET form an electrical bridge network. The advantage of this configuration is grounding the reference electrode Ref, so that the only one reference electrode is necessary for multiple ISFET detection. The circuit has a wide range of operations and is suitable for ISFETs with unspecified characteristics. However, the Zener diode ZN1 needs a special manufacture technology, and the voltages of its two sides are floating. The circuit in FIG. 3 is not suitably implemented by a standard CMOS technology.

SUMMARY OF THE INVENTION

The main object of the invention is to provide an ion sensing circuit that grounds the reference electrode and bridge-type sensing circuit with a floating reference voltage source. The disclosed circuit can be implemented or mass manufactured with integrated circuits by CMOS technology, which is the main bottleneck of the prior art, and is also applicable to sensor arrays.

To achieve the objects of the invention, the disclosed sensing circuit includes a bridge sensing circuit and a differential amplifying circuit. The bridge circuit senses the ion concentration in constant drain-source voltage and constant drain current mode of operation of the transistor ISFET. The differential amplifying circuit amplifies the output of the bridge type sensing circuit and stabilizes the transistor ISFET drain-source voltage VDS and drain current IDS due to feedback loop operation of the amplifier and constant value floating reference voltage that supplies the bridge.

A reference voltage generating circuit is also disclosed by the invention for generating the reference voltage Vref. The reference voltage generating circuit is composed of a plurality of resistors, an amplifier, and a Zener diode such that parts of the components can be manufactured by integrated circuit technology. In the second preferred embodiment of the reference voltage generating circuit, the reference voltage generating circuit includes a plurality of resistors, an amplifier, and bipolar junction transistors. All the components in the second embodiment can be implemented by integrated circuits.

The disclosed sensing circuit is able to acquire signals from enhancement or depletion mode type ISFET-based sensors or sensor arrays with no switching time delay and in wide operation range, no matter whether the sensing membranes of the ISFETs are known or unknown. Meanwhile, only one reference electrode is needed for the disclosed sensing circuit such that the circuit is easily implemented by CMOS technology. The circuit can be also applied to the ISFET-based multiple sensors or sensor arrays.

Furthermore, the disclosed ion sensing circuit acquires all the ISFET signals with no switching delay time. The circuit also can be promoted to satisfy the industry demands in mass production of ISFETs for more rapid, stable and accurate detection of their characteristics.

Further scope of applicability of the invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 4:
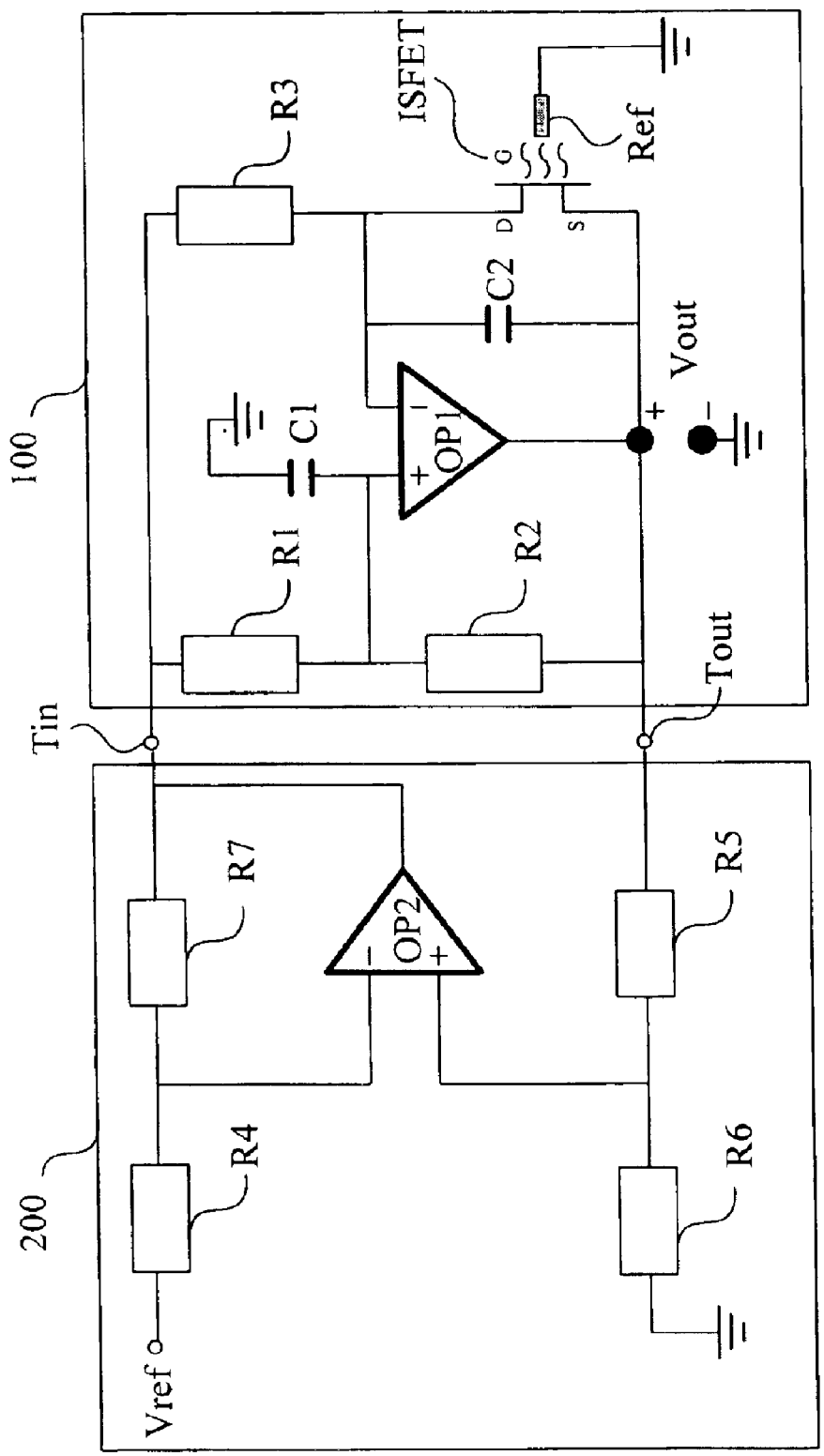
FIG. 4 is the ion sensing circuit of the first embodiment of the invention, with the characteristics of reference electrode grounding and bridge-type sensing circuit, and bridge-type floating reference voltage source.

FIG. 4 illustrates the ion sensing circuit of the invention. The circuit in FIG. 4 can be implemented by integrated circuits. Bridge architecture is adopted in the bridge sensing circuit, in which the reference electrode Ref is grounded and the source terminal of the transistor ISFET floats due to its threshold voltage variation, which is output signal Vout.

The disclosed sensor can be placed directly into a solution. When the analyte to be measured reacts with the sensing membrane, the variation of the electric potential at the interface sensing membrane/solution results in changes of the gate-source voltage of the transistor ISFET and output signal Vout. The transistor ISFET is one kind of ion sensing element, which modulates the resistance of the channel between the drain and the source due to changes of the ion concentration in the solution.

As shown in FIG. 4, the bridge sensing circuit 100 is a bridged type circuit, which is composed of a first impedance element R1, a second impedance element R2, a third impedance element R3, an Ion-Sensitive Field Effect Transistor ISFET, and a first amplifier OP1. The first amplifier OP1 is one kind of operational amplifier. The first impedance element R1 and the second impedance element R2 are connected in serial, and the third impedance element R3 and the transistor ISFET are connected in serial. The two serial circuits are connected in parallel. The positive terminal of the first amplifier OP1 is coupled between the first impedance element R1 and the second impedance element R2, while the negative one is coupled between the third impedance element R3 and the drain terminal of the transistor ISFET. The output terminal of the first amplifier OP1 is coupled between the second impedance element R2 and the source terminal of the transistor ISFET. The reference electrode Ref is connected to the ground. Since the output signal Vout is measured between ground and the source terminal of the transistor ISFET, the source terminal is floating. Compared with the prior art, not only the disclosed circuit but also the multiple sensing circuit need only single reference electrode to detect the concentration of several analytes.

Owing to the balanced condition of the bridge network and the virtual short circuit of the input terminals of the operational amplifier, the constant voltage VDS of the transistor ISFET is generated, and the constant current IDS through the transistor ISFET is determined by the third impedance element R3. Therefore, the transistor ISFET is operating in the constant drain-source voltage and constant drain current conditions.

The drain of the transistor ISFET is connected through the third impedance element R3 to the terminal Tin, while its source terminal is connected to Tout. The differential amplifying circuit 200 is composed of a second amplifier OP2 and four impedance elements R4, R5, R6 and R7. The second amplifier OP2 is one kind of operational amplifier.

A first capacitor C1 is coupled between the positive terminal of the first amplifier OP1 and the ground, while a second capacitor C2 is coupled between the negative terminal of the first amplifier OP1 and the output terminal Tout. Both capacitors are used as bypass capacitors.

The two input voltages of the differential amplifying circuit 200 are the reference voltage Vref, which is fed to the negative terminal of the amplifier OP2 via the fourth impedance element R4, and the output voltage Vout from the bridge sensing circuit 100, which is fed to the positive terminal of the amplifier OP2 via the fifth impedance element R5. The sixth impedance element R6 is coupled between the positive terminal of the second amplifier OP2 and the ground. The seventh impedance element R7 is coupled between the negative terminal and the output terminal of the amplifier OP2.

The transistor ISFET operates in the constant drain-source voltage and drain current mode, in which the conversion of chemical signal to electric one has the highest accuracy. Compared with the prior art, the invention adopts a differential amplifying circuit 200 to couple with the bridge sensing circuit 100, whose the balance condition causes the transistor ISFET to operate in the constant drain-source voltage and constant drain current mode, thereby detecting the accurate electrolyte concentration.

Figure 5:
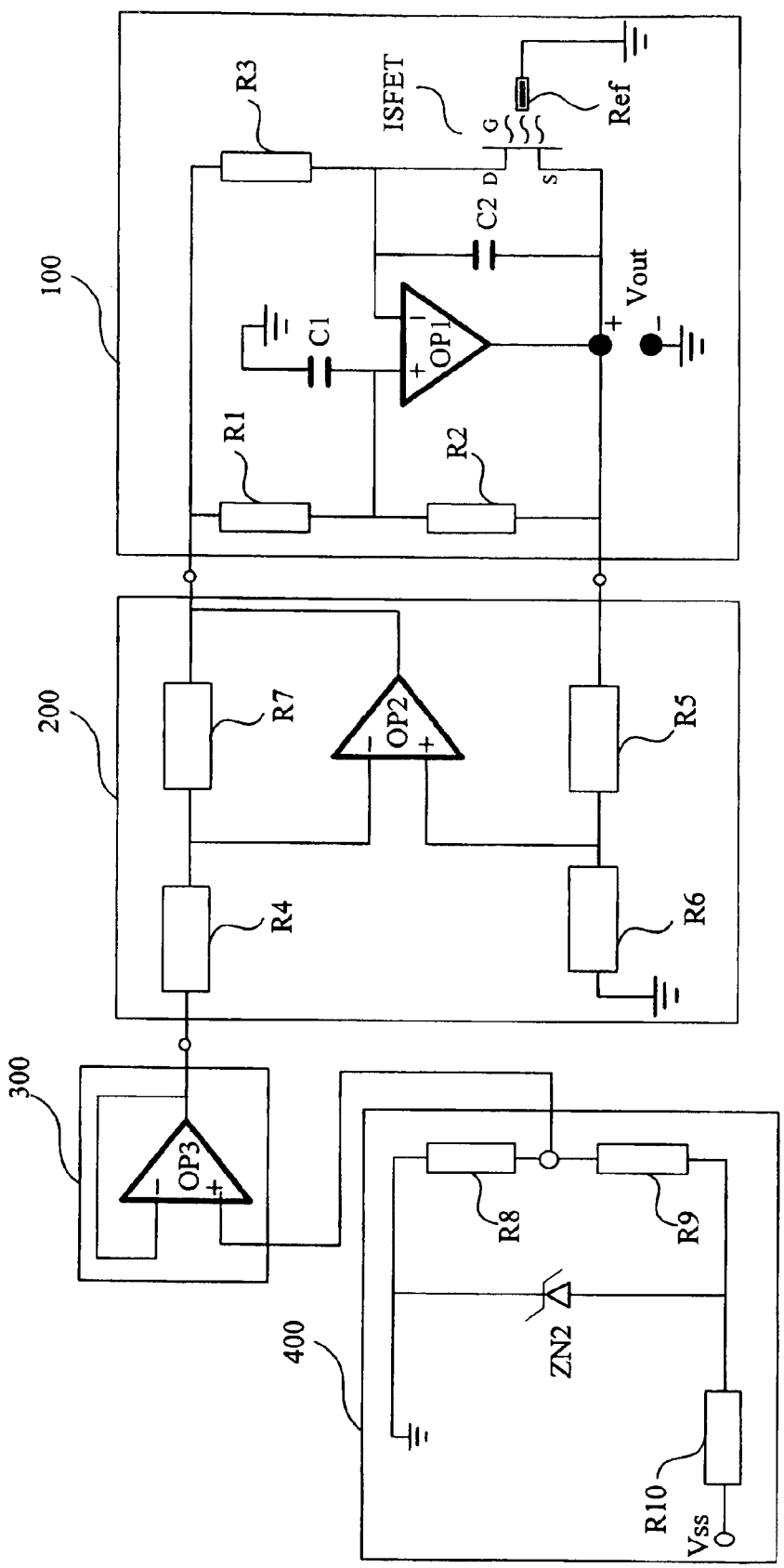
FIG. 5 is the reference voltage generating circuit accompanying the first embodiment of the invention.

The voltage generating circuit 400 is illustrated in FIG. 5. Besides the bridge sensing circuit 100 and the differential amplifying circuit 200, the circuit in FIG. 5 further includes a follower type impedance converter circuit 300 and a voltage generating circuit 400. The voltage generating circuit 400 delivers constant voltage, which is amplified as the reference voltage Vref of FIG. 4 by the follower type impedance converter circuit 300. The follower type impedance converter circuit 300 is composed of a third amplifier OP3, which is one kind of operational amplifier. The output terminal of the amplifier OP3 is fed back to its negative terminal. The voltage generating circuit 400 includes a Zener diode ZN2. A tenth impedance element R10 is connected in serial between the P type side of the diode ZN2 and a negative voltage source Vss. An eighth impedance element R8 is connected between the N type side and the positive terminal of the third amplifier OP3, while a ninth impedance element R9 is connected between the P type side and the positive terminal of the third amplifier OP3. Both of the impedance elements R8 and R9 create a voltage divider.

Figure 1:
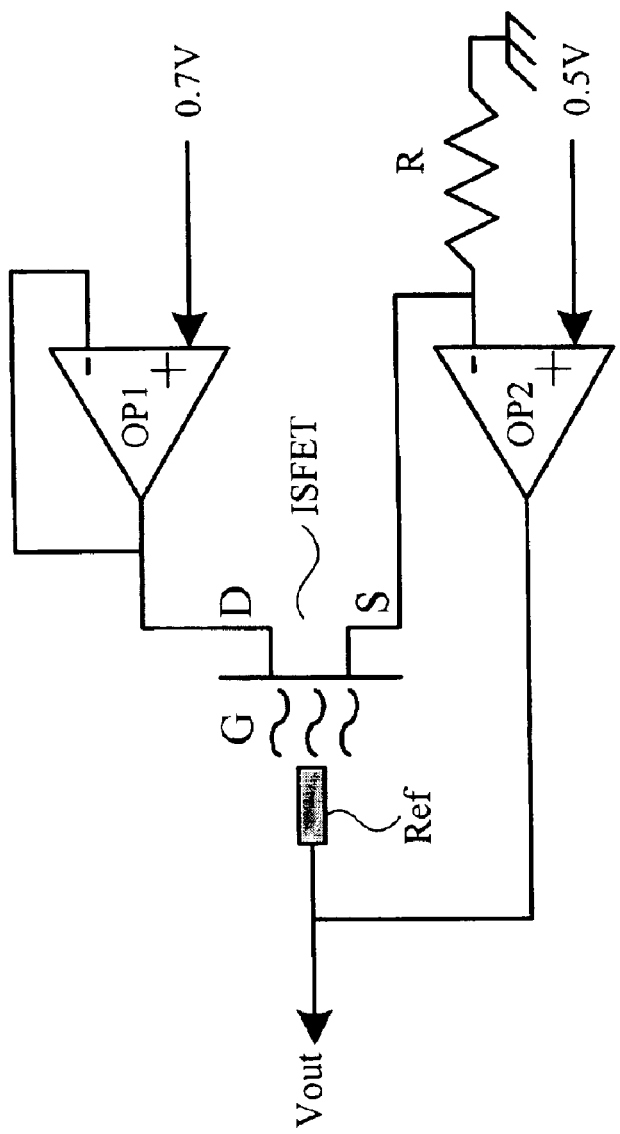
FIG. 1 is the sensing circuit of the prior art, whose characteristics include constant drain-source voltage, constant drain current, and floating reference electrode.
Figure 2:
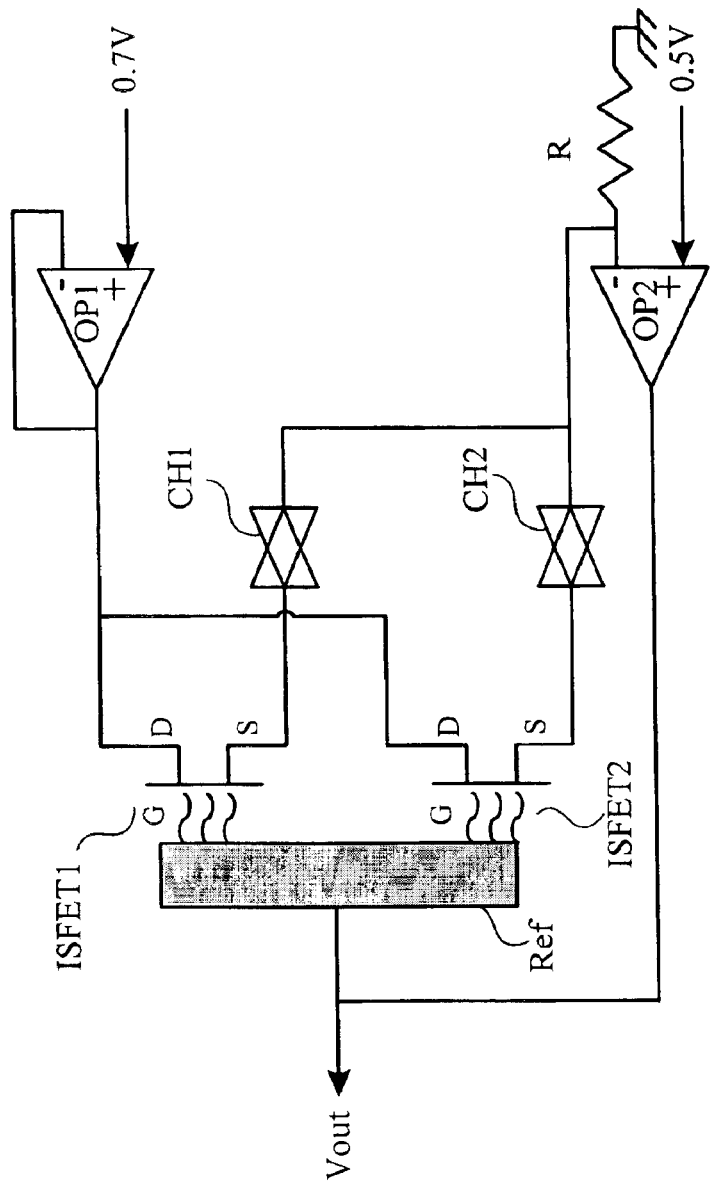
FIG. 2 is another sensing circuit of the prior art, whose characteristics include electrode.
Figure 3:
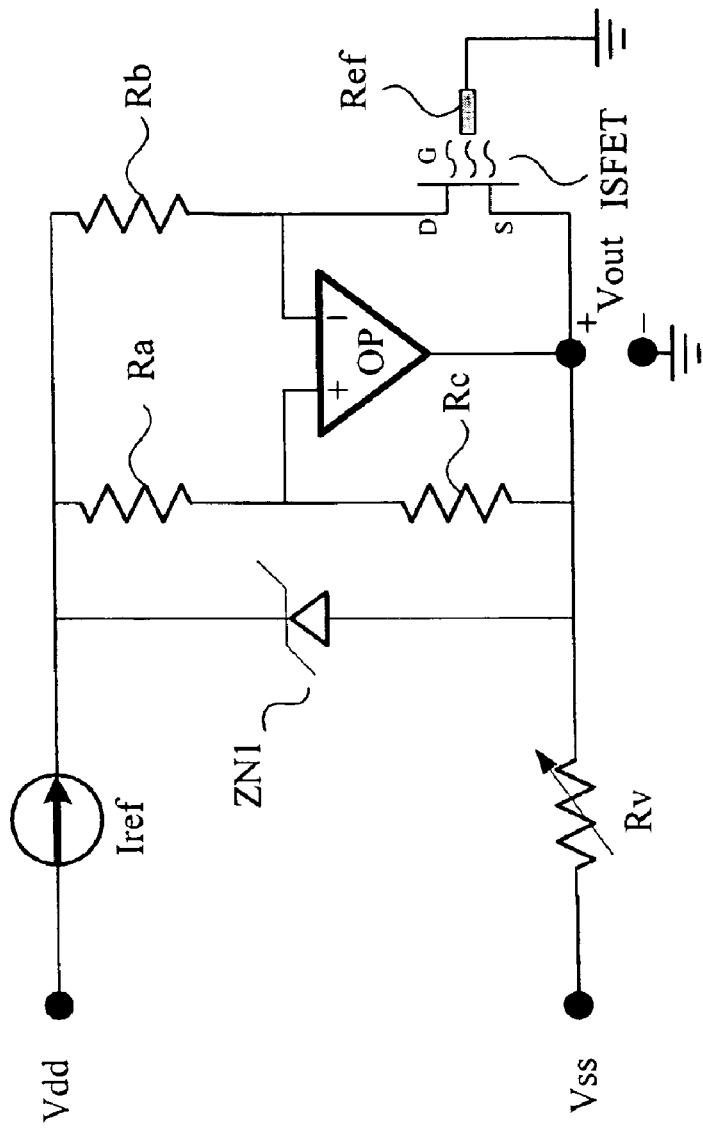
FIG. 3 is the sensing circuit of the prior art, whose characteristics include constant drain-source voltage, constant drain current, and bridge-type sensing circuit with floating reference voltage, and grounded reference electrode.

The N type side of the diode ZN2 in the voltage generating circuit 400 is connected with the ground, while the P type side is connected with a negative source Vss. Comparing the circuit 400, in which one side of the diode ZN2 is connected to the ground, with the prior art presented in FIG. 3, where both sides of the Zener diode ZN1 are floating, the generated voltage of the invention is more stable, and is amplified by the follower type impedance converter circuit 300, as the reference voltage for the differential amplifying circuit 200. The drawback of not being manufactured by CMOS technology of Zener diode ZN1 is thus avoided.

In the application of multiple sensors or sensor arrays, only one sensing circuit and only one reference electrode are needed for all ISFETs. Each ISFET has an independent signal reading circuit. The signals from multiple sensors or sensor arrays with unspecified sensing membranes could be acquired without delay of switching time.

Figure 6:
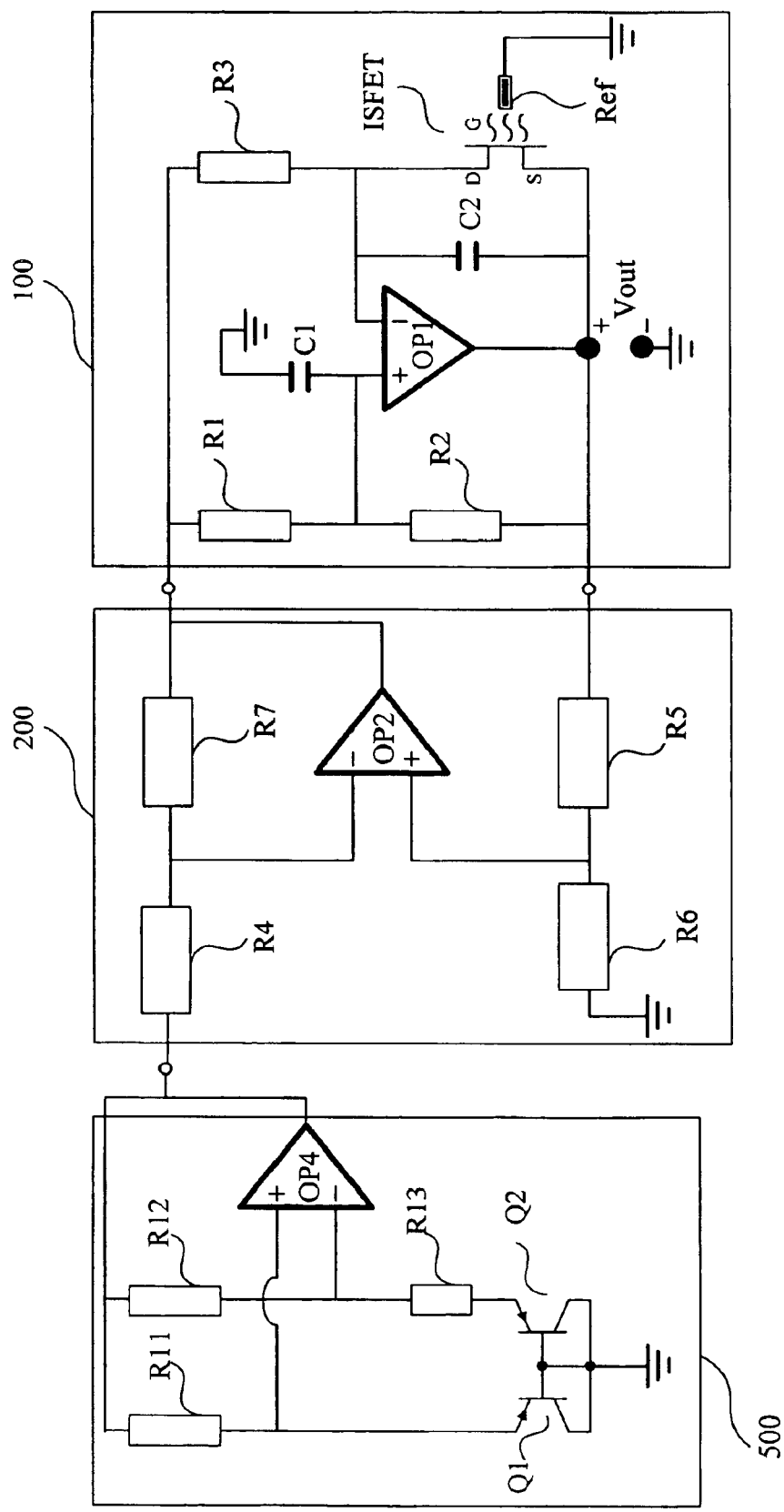
FIG. 6 is the sensing circuit of the second embodiment of the invention, with the characteristics of reference electrode grounding and bridge-type sensing circuit, and bridge-type floating reference voltage source with the bandgap voltage reference circuit.

FIG. 6 illustrates the second embodiment of the invention. Besides the advantages of circuit shown in FIGS. 4 and 5, the circuit in FIG. 6 is totally implemented by integrated circuit, and is economically viable.

The voltage generating circuit 500, which is one kind of bandgap voltage reference circuit, includes a first bipolar junction transistor Q1, and a second bipolar junction transistor Q2. The base terminals of the two transistors are connected with each other and connected to the ground. The collector terminals of the two transistors are connected to the ground. The emitter terminal of the first transistor Q1 is coupled to the positive terminal of the fourth amplifier OP4. The emitter terminal of the second transistor Q2 is coupled to the negative terminal of the fourth amplifier OP4 via a thirteenth impedance element R13. An eleventh impedance element R11 is connected between the output terminal and the positive terminal of the fourth amplifier OP4, while a twelfth impedance element R12 is connected between the output terminal and the negative terminal of the fourth amplifier OP4.

The second embodiment shown in FIG. 6 employs a bandgap voltage reference circuit to produce a stable voltage, which is independent of temperature and the voltage source. The differential amplifying circuit and the bridge sensing circuit are also included such that all the circuits can be implemented by integrated circuits, thereby forming an ISFET signal readout circuit with the features of a grounding reference electrode and floating source terminal. Once the disclosed voltage generating circuit in FIG. 6 is applied to the sensing array circuit, only one bandgap voltage reference circuit of the second embodiment is needed.

Nowadays to satisfy biomedical application a large number of simultaneously operating sensors is required. The disclosed ion sensing circuit enables multisensing measurement by ISFETs with improved reliability and stability. The main feature of the disclosed circuit is a bridge-type floating voltage source with wide operation range. The circuit is easily implemented by CMOS technology. The disclosed sensing circuit is able to acquire signals from enhancement or depletion mode type ISFET-based sensors or sensor arrays with no switching time delay and wide operation range, no matter whether the sensing membranes of ISFETs are specified and unspecified. Compared with the conventional circuits using floating gates-source voltage, because in the disclosed sensing circuit the reference electrode is grounded, which means that only one reference electrode is needed for ISFET-based multiple sensors or sensor arrays.

Furthermore, the disclosed ion sensing circuit acquires all ISFET signals with no switching delay time. The circuit can also be promoted to satisfy the industry demands in mass production of ISFETs for more rapid, stable and accurate detection of their characteristics.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An electronic circuit for ion sensor, comprising:
    a bridge sensing circuit comprising an input terminal and a sensing output terminal, for sensing ion concentration of a solution, wherein the bridge sensing circuit comprises an ion sensing element, which has a reference electrode coupled to a ground, and one terminal of which coupled to the sensing output terminal for delivering the signal of ion concentration; and
    a differential amplifying circuit, where a reference voltage is inputted into one input terminal of the differential amplifying circuit, while the other input terminal is coupled to the sensing output terminal of the bridge sensing circuit for delivering a differential voltage to the input terminal of the bridge sensing circuit such that the ion sensing element senses the ion concentration under the conditions of constant current and constant voltage;

wherein the bridge sensing circuit further comprises:
a first amplifier;
a first impedance element, coupled between the input terminal of the bridge sensing circuit and the positive terminal of the first amplifier;
a second impedance element, coupled between the positive terminal and the output terminal of the first amplifier;
a third impedance element, coupled to the input terminal of the bridge sensing circuit and the negative terminal of the first amplifier thereby determining the constant current;
wherein the first amplifier, the first impedance element, the second impedance element, the third impedance element, and the ion sensing element constitute a bridge network such that the ion sensing element operates under the conditions of constant drain-source voltage and constant drain current; and
wherein the ion sensing element is an ISFET, whose drain terminal is coupled to the negative terminal of the first amplifier, the source terminal is coupled to the output terminal of the first amplifier, and the reference electrode is coupled to a ground.

2. The electronic circuit for ion sensor of claim 1, wherein a first capacitor is further coupled between the positive terminal of the first amplifier and the ground terminal.

3. The electronic circuit for ion sensor of claim 1, wherein a second capacitor is further coupled between the negative terminal and the output terminal of the first amplifier.

4. The electronic circuit for ion sensor of claim 1, wherein the differential amplifying circuit further comprises:
a second amplifier, whose output terminal is coupled to the input terminal of the bridge sensing circuit;
a fourth impedance element, which is coupled between the negative terminal of the second amplifier and the reference voltage;
a fifth impedance element, which is coupled between the sensing output terminal of the bridge sensing circuit and the positive terminal of the second amplifier;
a sixth impedance element, which is coupled between the positive terminal of the second amplifier and a ground; and
a seventh impedance element, which is coupled between the output terminal and the negative terminal of the second amplifier.

5. An electronic circuit for ion sensor, comprising:
a bridge sensing circuit which has an input terminal and a sensing output terminal, for sensing ion concentration of a solution, wherein the bridge sensing circuit comprises an ion sensing element, which has a reference electrode coupled to a ground, and one terminal of which coupled to the sensing output terminal for delivering the ion concentration;
a voltage generating circuit for generating a constant voltage according to a negative voltage source;
a follower type impedance converter circuit for amplifying the constant voltage as a reference voltage;
a differential amplifying circuit, the reference voltage being inputted into one input terminal of which circuit, the other input terminal being coupled to the sensing output terminal of the bridge sensing circuit for delivering a differential voltage to the input terminal of the bridge sensing circuit such that the ion sensing element senses the ion concentration under the conditions of constant drain current and constant drain-source voltage;

wherein the bridge sensing circuit further comprises:
a first amplifier;
a first impedance element, coupled between the input terminal of the bridge sensing circuit and the positive terminal of the first amplifier;
a second impedance element, coupled between the positive terminal and the output terminal of the first amplifier;
a third impedance element, coupled to the input terminal of the bridge sensing circuit and the negative terminal of the first amplifier thereby determining the constant current;
wherein the first amplifier, the first impedance element, the second impedance element, the third impedance element, and the ion sensing element constitute a bridge network such that the ion sensing element operates under the conditions of constant voltage and constant current;
wherein the ion sensing element is an ion-sensitive field effect transistor, whose drain terminal is coupled to the negative terminal of the first amplifier, the source terminal is coupled to the output terminal of the first amplifier, and the reference electrode is coupled to a around.

6. The electronic circuit for ion sensor of claim 5, wherein the ion sensing element is an ion-sensitive field effect transistor, whose drain terminal is coupled to the negative terminal of the first amplifier, the source terminal is coupled to the output terminal of the first amplifier, and the reference electrode is coupled to a ground.

7. The electronic circuit for ion sensor of claim 5, wherein a first capacitor is further coupled between the positive terminal of the first amplifier and the ground terminal.

8. The electronic circuit for ion sensor of claim 5, wherein a second capacitor is further coupled between the negative terminal and the output terminal of the first amplifier.

9. The electronic circuit for ion sensor of claim 5, wherein the differential amplifying circuit further comprises:
a second amplifier, whose output terminal is coupled to the input terminal of the bridge sensing circuit;
a fourth impedance element, which is coupled between the negative terminal of the second amplifier and the reference voltage terminal;
a fifth impedance element, which is coupled between the sensing output terminal of the bridge sensing circuit and the positive terminal of the second amplifier;
a sixth impedance element, which is coupled between the positive terminal of the second amplifier and a ground; and
a seventh impedance element, which is coupled between the output terminal and the negative terminal of the second amplifier.

10. The electronic circuit for ion sensor of claim 5, the follower type impedance converter circuit further comprises a third amplifier.

11. The electronic circuit for ion sensor of claim 5, wherein the voltage generating circuit comprises a Zener diode, whose N electrode is coupled to the ground, and P electrode is coupled to the negative voltage source.

12. The electronic circuit for ion sensor of claim 5, wherein an eighth impedance element is further coupled between the positive terminal of a third amplifier and the N electrode of a Zener diode.

13. The electronic circuit for ion sensor of claim 5, wherein a ninth impedance element is further coupled between the positive terminal of a third amplifier and the P electrode of a Zener diode.

14. The electronic circuit for ion sensor of claim 5, wherein a tenth impedance is further coupled between the P electrode of a Zener diode and the negative voltage source.

15. The electronic circuit for ion sensor of claim 5, wherein a bandgap reference voltage generating circuit further comprises a first bipolar junction transistor, a second bipolar junction transistor, a fourth amplifier and the thirteen impedance element, the base terminals of the transistors are coupled with each other and to a ground, the collector terminals are coupled to the ground, the emitter terminal of the first bipolar junction transistor is coupled to the positive terminal of the fourth amplifier, the emitter terminal of the second bipolar junction transistor is coupled to the terminal of the thirteen impedance element and to the negative terminal of the fourth amplifier.

16. The electronic circuit for ion sensor of claim 15, wherein an eleventh impedance element is further coupled between the positive terminal and the output terminal of the fourth amplifier.

17. The electronic circuit for ion sensor of claim 15, wherein a twelfth impedance element is further coupled between the negative terminal and the output terminal of the fourth amplifier.

18. An electronic circuit for ion sensor, comprising:
   a bridge sensing circuit which has an input terminal and a sensing output terminal, for sensing ion concentration of a solution, wherein the bridge sensing circuit comprises an ion sensing element, which has a reference electrode coupled to a ground, and one terminal of which coupled to the sensing output terminal for delivering the ion concentration;
   a voltage generating circuit for generating a constant voltage according to a negative voltage source;
   a follower type impedance converter circuit for amplifying the constant voltage as a reference voltage;
   a differential amplifying circuit, the reference voltage being inputted into one input terminal of which circuit, the other input terminal being coupled to the sensing output terminal of the bridge sensing circuit for delivering a differential voltage to the input terminal of the bridge sensing circuit such that the ion sensing element senses the ion concentration under the conditions of constant drain current and constant drain-source voltage;
   wherein the voltage generating circuit comprises a Zener diode, whose N electrode is coupled to the ground, and P electrode is coupled to the negative voltage source.

19. The electronic circuit for ion sensor of claim 18, wherein the bridge sensing circuit further comprises:
   a first amplifier;
   a first impedance element, coupled between the input terminal of the bridge sensing circuit and the positive terminal of the first amplifier;
   a second impedance element, coupled between the positive terminal and the output terminal of the first amplifier;
   a third impedance element, coupled to the input terminal of the bridge sensing circuit and the negative terminal of the first amplifier thereby determining the constant current;
   wherein the first amplifier, the first impedance element, the second impedance element, the third impedance element, and the ion sensing element constitute a bridge network such that the ion sensing element operates under the conditions of constant voltage and constant current.

* * * * *